(12) United States Patent
Sood et al.

(10) Patent No.: US 9,810,641 B2
(45) Date of Patent: Nov. 7, 2017

(54) SYSTEMS AND METHODS FOR MEASURING PHYSICAL CHARACTERISTICS OF SEMICONDUCTOR DEVICE ELEMENTS USING STRUCTURED LIGHT

(71) Applicant: Kulicke & Soffa Industries, Inc., Fort Washington, PA (US)

(72) Inventors: Deepak Sood, New Britain, PA (US); Zhijie Wang, Chalfont, PA (US); Thomas J. Colosimo, Jr., West Chester, PA (US); David A. Rauth, Riverton, NJ (US); Shu-Guo Tang, Chalfont, PA (US)

(73) Assignee: Kulicke & Soffa Industries, Inc., Fort Washington, PA (US)

( * ) Notice: Subject to any disclaimer, the term of this patent is extended or adjusted under 35 U.S.C. 154(b) by 0 days.

(21) Appl. No.: 14/469,830

(22) Filed: Aug. 27, 2014

(65) Prior Publication Data
US 2015/0059957 A1 Mar. 5, 2015

Related U.S. Application Data

(60) Provisional application No. 61/873,288, filed on Sep. 3, 2013.

(51) Int. Cl.
*G01N 21/95* (2006.01)
*G01N 21/88* (2006.01)
(Continued)

(52) U.S. Cl.
CPC ..... *G01N 21/9501* (2013.01); *G01N 21/8422* (2013.01); *G01N 21/8806* (2013.01);
(Continued)

(58) Field of Classification Search
CPC .......... G01N 21/9501; G01N 21/8422; G01N 21/8806; H01L 22/12; H01L 2224/27312; H01L 2224/812; H01L 2224/81203
(Continued)

(56) References Cited

U.S. PATENT DOCUMENTS 8,224,070 B2 7/2012 Umemura et al.
2005/0095744 A1* 5/2005 Shi .................. H01L 21/563
438/106
(Continued)

FOREIGN PATENT DOCUMENTS

CN 1968598 5/2007
CN 101929850 12/2010
(Continued)

*Primary Examiner* — George Koch
(74) *Attorney, Agent, or Firm* — Stradley Ronon Stevens & Young, LLP

(57) ABSTRACT

A method of determining a physical characteristic of an adhesive material on a semiconductor device element using structured light is provided. The method includes the steps of: (1) applying a structured light pattern to an adhesive material on a semiconductor device element; (2) creating an image of the structured light pattern using a camera; and (3) analyzing the image of the structured light pattern to determine a physical characteristic of the adhesive material. Additional methods and systems for determining physical characteristics of semiconductor devices and elements using structured light are also provided.

13 Claims, 7 Drawing Sheets

(51) Int. Cl.
*H01L 21/66* (2006.01)
*G06T 7/00* (2017.01)
*G01N 21/84* (2006.01)
*H01L 23/00* (2006.01)

(52) U.S. Cl.
CPC ............ *G06T 7/0006* (2013.01); *H01L 22/12* (2013.01); *H01L 24/75* (2013.01); *H01L 24/83* (2013.01); *G01N 2021/8812* (2013.01); *G01N 2021/8829* (2013.01); *G06T 2207/10152* (2013.01); *G06T 2207/30148* (2013.01); *H01L 24/16* (2013.01); *H01L 24/27* (2013.01); *H01L 24/29* (2013.01); *H01L 24/73* (2013.01); *H01L 24/81* (2013.01); *H01L 24/92* (2013.01); *H01L 2224/16145* (2013.01); *H01L 2224/16225* (2013.01); *H01L 2224/2731* (2013.01); *H01L 2224/29012* (2013.01); *H01L 2224/2919* (2013.01); *H01L 2224/32145* (2013.01); *H01L 2224/32225* (2013.01); *H01L 2224/73204* (2013.01); *H01L 2224/75901* (2013.01); *H01L 2224/81203* (2013.01); *H01L 2224/83191* (2013.01); *H01L 2224/83192* (2013.01); *H01L 2224/83203* (2013.01); *H01L 2224/83908* (2013.01); *H01L 2224/92125* (2013.01); *H01L 2924/3511* (2013.01); *H01L 2924/3512* (2013.01)

(58) Field of Classification Search
USPC .............. 156/56, 367, 378; 348/87
See application file for complete search history.

(56) References Cited

U.S. PATENT DOCUMENTS

| | | |
|---|---|---|
| 2006/0204074 A1 | 9/2006 | Moriya et al. |
| 2007/0115482 A1* | 5/2007 | Harding ............... G01B 11/306 356/600 |
| 2007/0120977 A1* | 5/2007 | Duquette ........... H04N 13/0207 348/87 |
| 2009/0025972 A1* | 1/2009 | Nishida ................ H05K 3/3494 174/263 |
| 2009/0120589 A1* | 5/2009 | Kang ................ H01L 21/67144 156/539 |
| 2010/0183194 A1* | 7/2010 | Umemura .......... G01B 11/0608 382/103 |
| 2010/0188400 A1* | 7/2010 | Chen .................... G06T 7/0057 345/420 |
| 2012/0040477 A1* | 2/2012 | Yu .......................... H01L 22/20 438/15 |
| 2012/0070939 A1 | 3/2012 | Dunne et al. |

FOREIGN PATENT DOCUMENTS

| | | |
|---|---|---|
| JP | 2000077812 A * | 3/2000 |
| KR | 10-2012-0123933 | 11/2012 |
| TW | 200700716 | 1/2007 |
| TW | M345227 | 11/2008 |
| TW | 201030308 | 8/2010 |
| WO | 03043400 | 5/2003 |

* cited by examiner

SYSTEMS AND METHODS FOR MEASURING PHYSICAL CHARACTERISTICS OF SEMICONDUCTOR DEVICE ELEMENTS USING STRUCTURED LIGHT

CROSS-REFERENCE TO RELATED APPLICATION

This application claims the benefit of U.S. Provisional Application No. 61/873,288, filed Sep. 3, 2013, the contents of which are incorporated herein by reference.

FIELD OF THE INVENTION

The present invention relates to systems and methods for measuring physical characteristics of semiconductor device elements (often in connection with bonding operations of the semiconductor elements), and more particularly, to improved systems and methods for measuring such physical characteristics using structured light.

BACKGROUND OF THE INVENTION

Semiconductor devices include various physical features or characteristics that are desirably controlled. For example, typically it is desirable that semiconductor dice are substantially flat prior to packaging (e.g., prior to die attach processes, thermo-compressive bonding processes, etc.). Also, it is typical that certain physical attributes of elements included in a semiconductor device or package be measured to ensure conformity with design criteria or specifications.

Specifically, in thermo-compression bonding (e.g., bonding a semiconductor device to another semiconductor device with copper pillars or similar conductive structures between the devices), physical features or characteristics of the bonding elements are desirably controlled. This is particularly true in simultaneous thermo-compression bonding of many devices.

Thus, it would be desirable to provide improved systems for, and methods of, measuring and/or controlling such physical characteristics.

SUMMARY OF THE INVENTION

According to an exemplary embodiment of the present invention, a method of determining a physical characteristic of an adhesive material on a semiconductor device element using structured light is provided. The method includes the steps of: (1) applying a structured light pattern to an adhesive material on a semiconductor device element; (2) creating an image of the structured light pattern using a camera; and (3) analyzing the image of the structured light pattern to determine a physical characteristic of the adhesive material.

According to another exemplary embodiment of the present invention, a method of determining a physical characteristic of a fillet of an adhesive material applied between elements of a semiconductor device using structured light is provided. The method includes the steps of: (1) applying a structured light pattern to an adhesive fillet between elements of a semiconductor device; (2) creating an image of the structured light pattern using a camera; and (3) analyzing the image of the structured light pattern to determine a physical characteristic of the adhesive fillet.

According to yet another exemplary embodiment of the present invention, a method of determining a flatness characteristic of a semiconductor device using structured light is provided. The method includes: (1) creating an image of a structured light pattern reflected by a surface of a semiconductor device using a camera; and (2) analyzing the image of the structured light pattern to determine a flatness characteristic of the semiconductor device.

In accordance with certain exemplary embodiments of the present invention, these and other methods (including some or all of the steps recited herein) may be performed on a thermo-compression bonding machine.

In accordance with certain exemplary embodiments of the present invention, the methods described herein (including methods of determining a physical characteristic of an adhesive material on a semiconductor device element, methods of determining a physical characteristic of a fillet of an adhesive material applied between elements of a semiconductor device, and methods of determining a flatness characteristic of a semiconductor device) may involve using different structured light patterns to achieve the best measurement result (e.g., a physical characteristic or a flatness characteristic as described herein). For example, the steps of creating an image of a structured light pattern using a camera, and analyzing the image of the structured light pattern to determine a characteristic, may be repeated (thereby analyzing a plurality of images) to determine the desired measurement result.

According to yet another exemplary embodiment of the present invention, a thermo-compression bonding system is provided. The thermo-compression bonding system includes: (1) a support structure for supporting a semiconductor device element including an adhesive material; (2) a structured light source for providing a structured light pattern on the adhesive material; and (3) a camera for creating an image of the structured light pattern on the adhesive material.

According to yet another exemplary embodiment of the present invention, a thermo-compression bonding system is provided. The thermo-compression bonding system includes: (1) a support structure for supporting a semiconductor device; (2) a structured light source for providing a structured light pattern; and (3) a camera for indirectly viewing the structured light pattern using a reflective surface of the semiconductor device, the camera generating an image of the structured light pattern.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures.

DETAILED DESCRIPTION OF THE INVENTION

Figure 1:
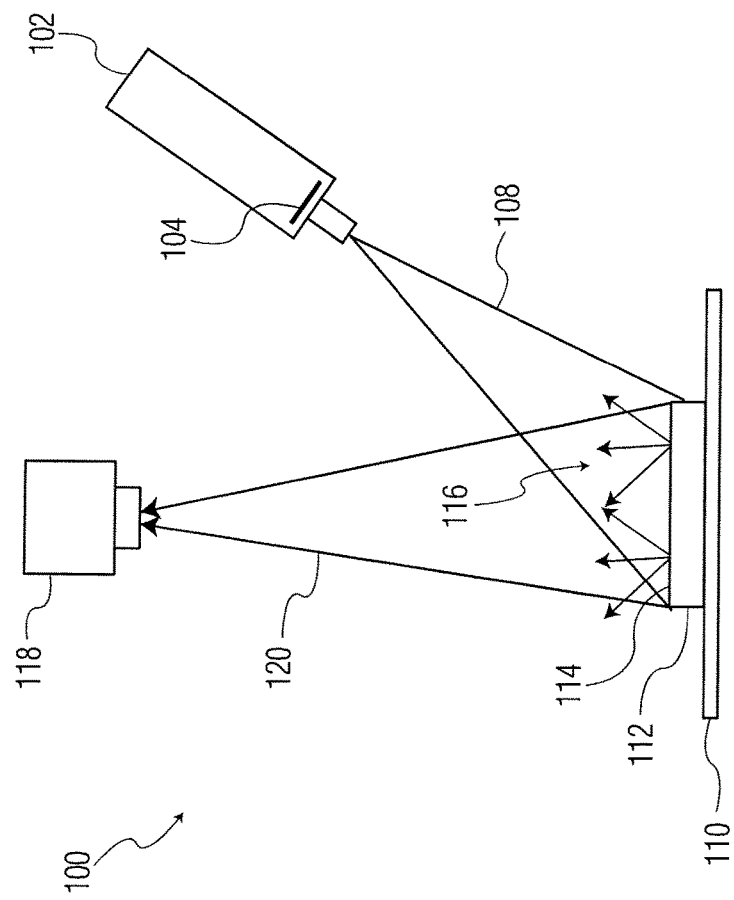
FIG. 1 is a block diagram view of elements of a thermo-compression bonding machine in accordance with an exemplary embodiment of the present invention.

As used herein, the term "structured light" is intended to be defined as is known to those skilled in the art, and specifically refers to light including a projection (e.g., a pattern, such as pixels with different gray levels in a grid or horizontal bar configuration) applied to a surface to be imaged.

In accordance with certain exemplary embodiments of the present invention, systems and methods for measuring (e.g., profiling, characterizing, etc.) elements of semiconductor devices using structured light are provided. Exemplary elements of semiconductor devices being measured include adhesive material between elements of the semiconductor device, a fillet of adhesive material between elements of the semiconductor device, and semiconductor device surfaces.

Adhesive material elements measured may include, for example, curable liquid materials such as epoxy, non-conductive paste, etc. Such adhesive materials may be applied between elements bonded together during thermo-compression bonding. More specifically, a first element of a semiconductor device, with conductive regions, may be provided on a support structure. An adhesive material may then be applied to this first element. Then, a second element (which may be semiconductor die or other device including conductive pillars or the like) is thereto-compressively bonded to the first element. This bonding may include, for example, heat and bond force. The adhesive material may be measured to determine, for example, a volume of the material (such as a 3D volume of the material), a distribution of the material (e.g., the pattern of the material), etc.

Aspects of the present invention may also be used to measure a fillet of adhesive material between such first and second elements. The fillet is the portion of the adhesive material that is exposed between the two elements (See, e.g., FIG. 4A). The fillet may be measured to determine, for example, a height of the fillet (reference number 410 in FIG. 4A), a length of the fillet (reference number 412 in FIG. 4A), a volume (e.g., a 3D volume of the fillet), amongst other quantities.

Aspects of the present invention may also be used to measure semiconductor device flatness characteristics. As will be appreciated by those skilled in the art, it is typically desirable that semiconductor devices (e.g., semiconductor die to be thereto-compressively bonded to another semiconductor element) are substantially flat and/or planar. The present invention may be used to determine if such devices are within a predetermined flatness specification (e.g., tolerance).

Aspects of the present invention may also be used to measure for semiconductor device crack characteristics including the size and location of such cracks.

As used herein, the term "semiconductor device" is intended to refer to any type of semiconductor device element including but not limited to bare semiconductor die, packaged semiconductor die, partially packaged semiconductor die, a region of a substrate to which a die will be bonded, a semiconductor wafer (or a portion thereof) including a plurality of semiconductor die, etc. Elements of a semiconductor device may include a semiconductor die, a substrate for supporting a semiconductor die, etc.

FIG. 1 illustrates elements of a thermo-compression bonding machine 100. Many elements have been omitted from FIG. 1 (and other machines illustrated herein) for clarity such as, for example, a bond head assembly, a material handling system, etc. Machine 100 includes a structured light source 102 (e.g., shown as, but not limited to, digital fringe projector 102). Light source 102 includes grating 104 or other structure (such as a DLP chip in a digital fringe projector embodiment). Light 108 transmitted from source 102 is structured light that includes a structured light pattern imposed on the light, for example, using grate 104. FIG. 1 also illustrates support structure 110 which supports element 112. Element 112 may be, for example, a semiconductor device to which an adhesive material (e.g., an epoxy material, a non-conductive paste, etc.—applied to the semiconductor device as a curable liquid) has been applied. The adhesive material includes a diffusive surface 114. When structured light 108 is received by diffusive surface 114, at least a portion of the resultant diffused light pattern 116 is imaged within field of view 120 of camera 118. The image generated by camera 118 may be used to measure a physical characteristic of the adhesive material (included in elements 112, 114) such as a volume or volume distribution. While element 112 is described as an adhesive material, other types of elements are contemplated such as substrates having a diffusive surface (or an at least partially diffusive surface).

Figure 2:
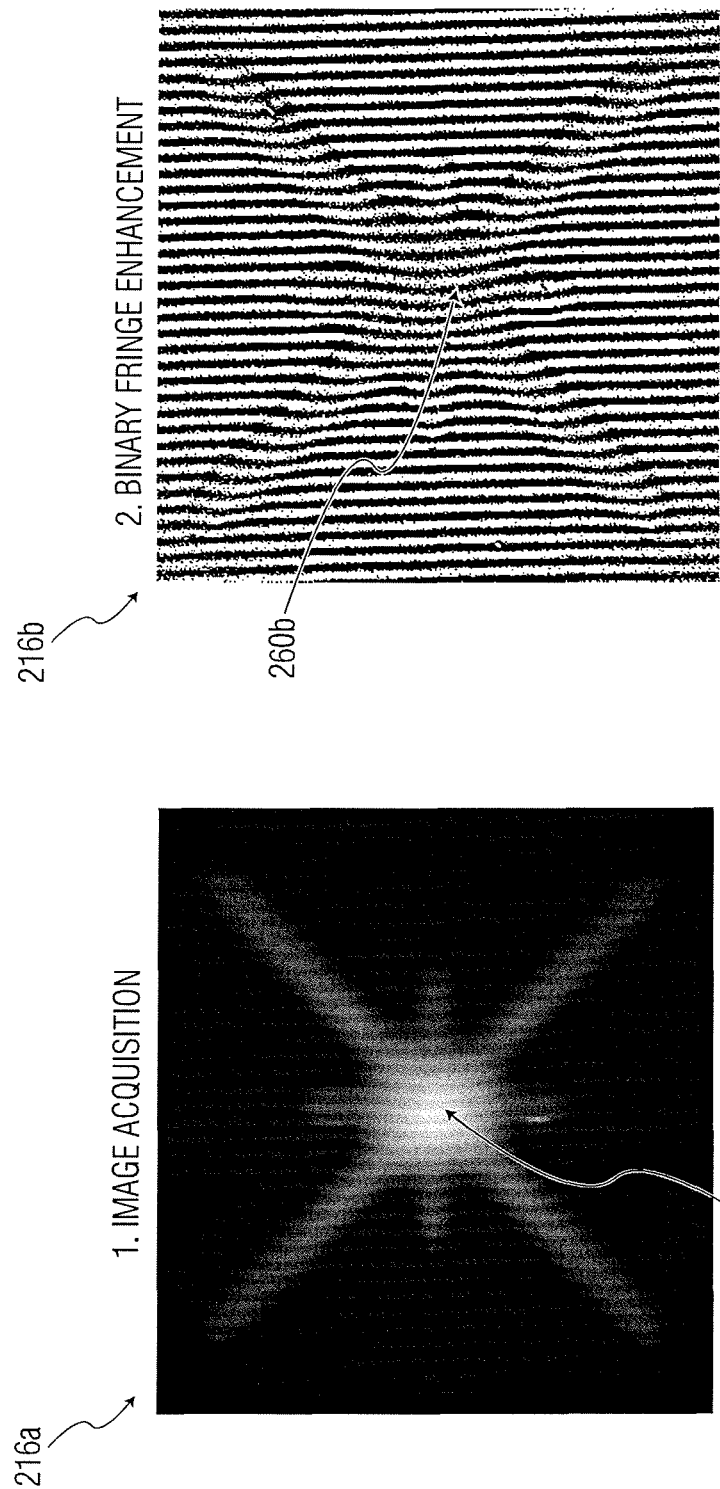
FIGS. 2A-2B are top views of an structured light patterns projected onto an adhesive material in accordance with an exemplary embodiment of the present invention.
Figure 3:
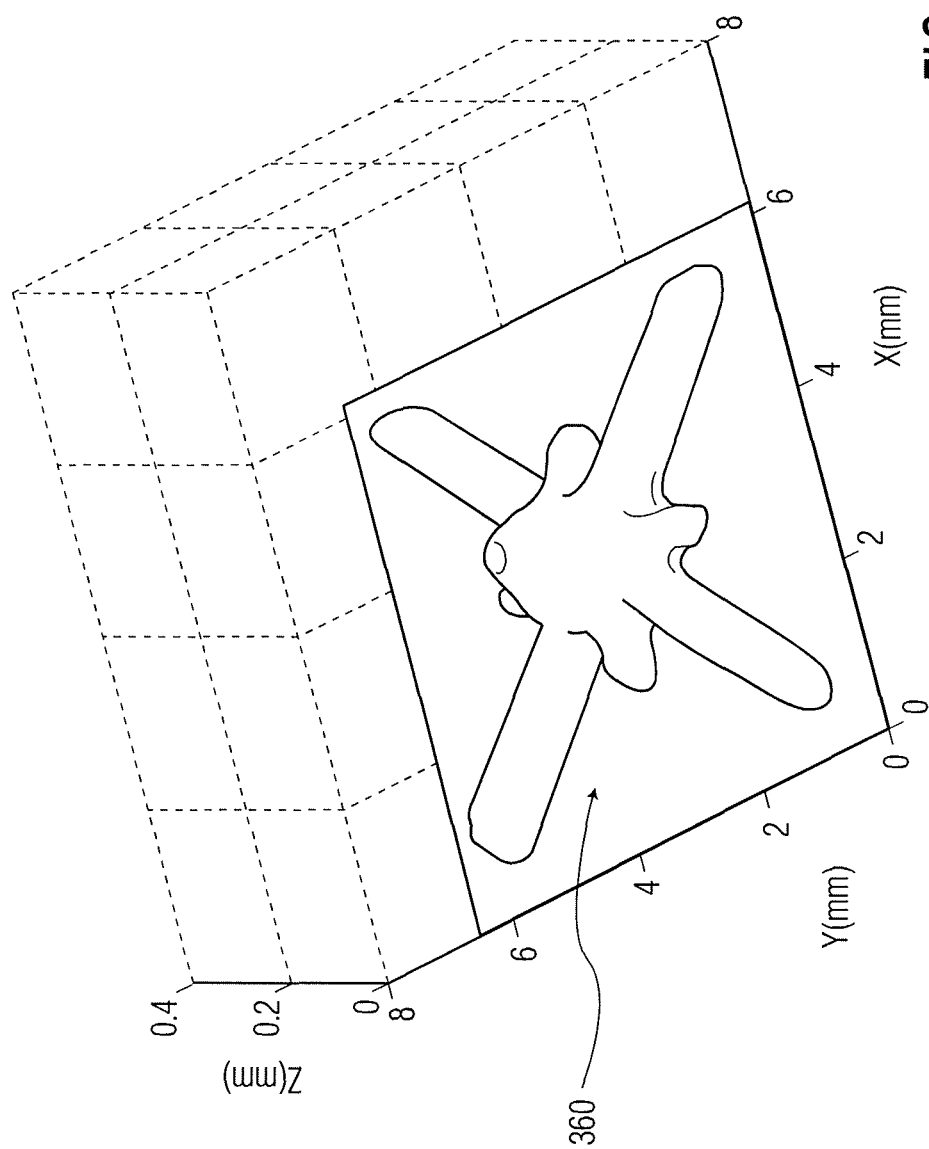
FIG. 3 is a three dimensional representation of an adhesive material generated in accordance with an exemplary embodiment of the present invention.

FIGS. 2A-2B illustrate two top view images 216a, 216b of adhesive material samples as applied to respective semiconductor devices. As illustrated, the adhesive material has a conventional "star" shaped or "burst" pattern. In FIG. 2A, the center portion 260a of the adhesive material sample is not very clear. In FIG. 2B, the image had been processed (e.g., using image processing hardware and/or software which may be included on a thermo-compression bonding machine) such that a clearer image is provided as in FIG. 2B. In FIG. 2B, the center portion 260b is much clearer than in FIG. 2A, and the structured light pattern (and the variation among the structured light lines in the pattern) is more visible. Using such an image, image processing hardware and/or software may be used to determine the desired physical characteristic which may be a simple characteristic (e.g., a number such as a volume) or a more complex physical characteristic such as a topographical map or representation. FIG. 3 illustrates an example of such a map 360.

Figure 4A:
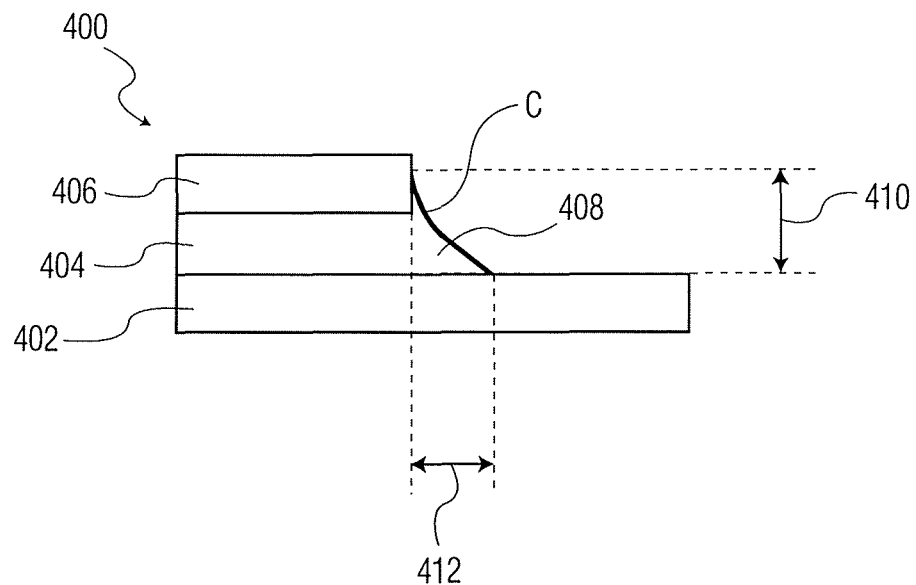
FIG. 4A is a block diagram side view of an adhesive material fillet to be imaged in accordance with an exemplary embodiment of the present invention.
Figure 4B:
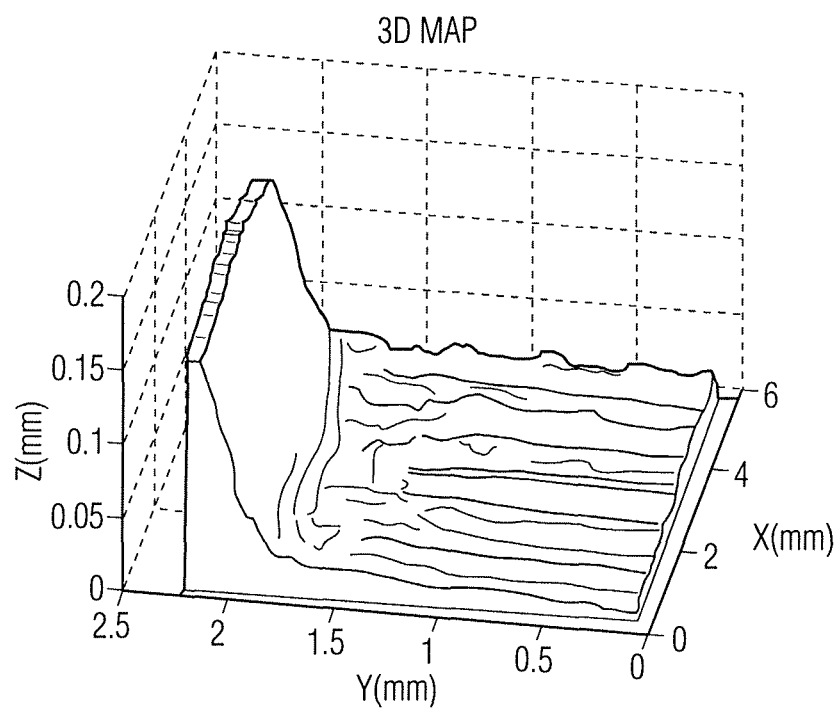
FIG. 4B is a three dimensional representation of an adhesive material fillet generated in accordance with an exemplary embodiment of the present invention.

The exemplary structured light imaging approach illustrated in FIG. 1 may be used to measure more than just a physical characteristic of an adhesive material such as shown in FIGS. 2A-2B. In another example, the light may be used to image (and thereby measure) a physical characteristic of an adhesive fillet. FIG. 4A illustrates a portion of semiconductor device 400 including a first semiconductor element 402 (e.g., a die or substrate), an adhesive layer 404 disposed on element 402, and a second semiconductor element 406 disposed on the adhesive layer 406. Fillet 408 (which is part of adhesive material 404) extends past an edge of element 406. It may be desirable to measure a physical characteristic of fillet 408 for example, height 410, length 412, or curvature "c". It may be useful to know such a characteristic in order to be confident that the adhesive material has not extended into areas where it should not extend. Of course, a more complex physical characteristic such as a topographical map or representation may be measured. FIG. 4B illustrates an example of such a map.

The physical characteristic of a fillet measured according to the present invention may include measuring the characteristic around the entire perimeter along which the fillet extends. For example, if a fillet extends around an entire edge of a semiconductor device, this entire fillet may be measured.

Figure 5:
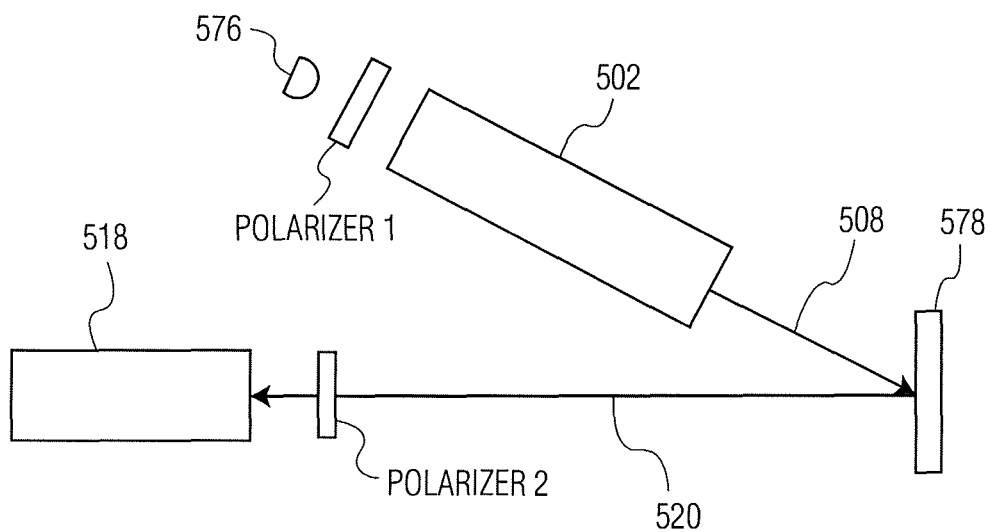
FIG. 5 is a block diagram view of imaging elements, which may be used in connection with a thermo-compression bonding machine, in accordance with an exemplary embodiment of the present invention.

In the images generated according to the present invention (e.g., using cameras, structured light, etc.)—various imaging complications may arise. One such complication relates to hot spots which may render the image less clear. FIG. 5 illustrates a configuration that may be useful to reduce such hot spots. More specifically, light source 576 (e.g., an LED or other source) is transmitted through polarizer 1, and into projection element 502 (e.g., including a grating or the like to generate a structured light image). The structured light 508 is diffused off of test sample 578 (e.g., adhesive material on a semiconductor device, etc.). A diffused image 520 is transmitted through polarizer 2 and is received by camera 518. The use of polarizers may be useful in reducing the effect of hot spots.

Figure 6:
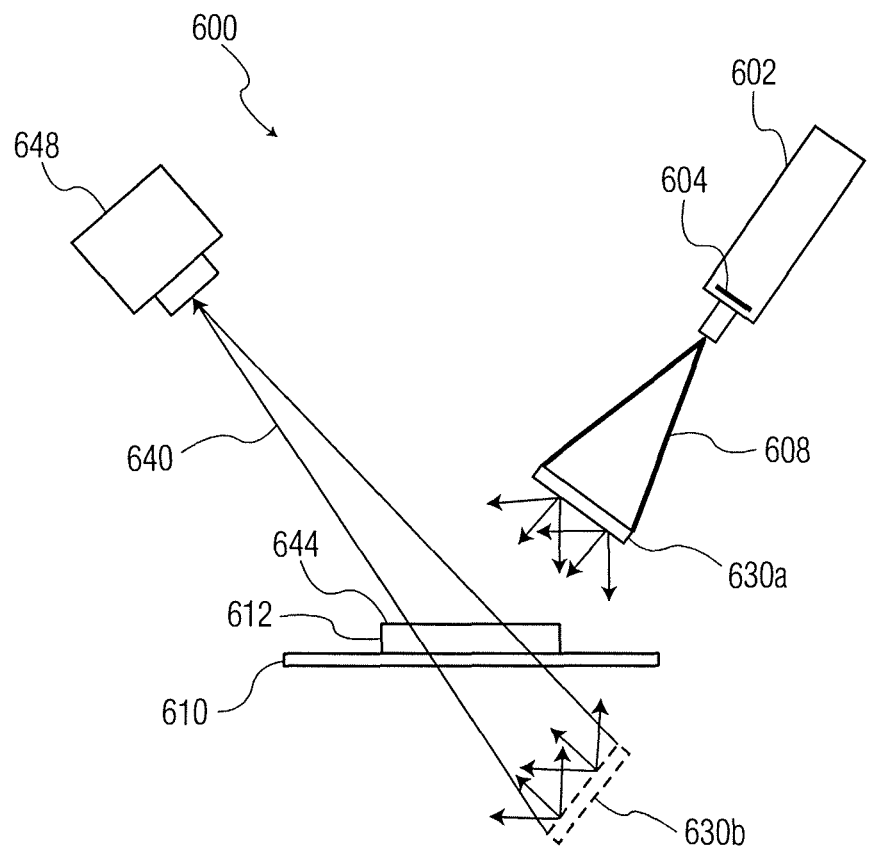
FIG. 6 is a block diagram view of elements of a thermo-compression bonding machine in accordance with an exemplary embodiment of the present invention.
Figure 7A:
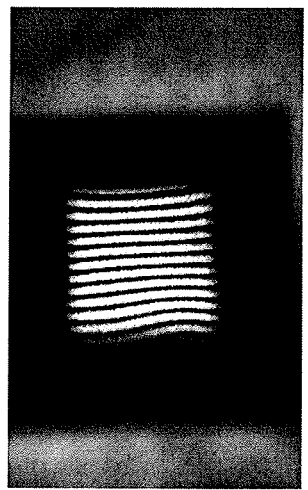
FIGS. 7A-7C are a series of images of a structured light patterns reflected from surfaces of semiconductor devices in accordance with an exemplary embodiment of the present invention.
Figure 7B:
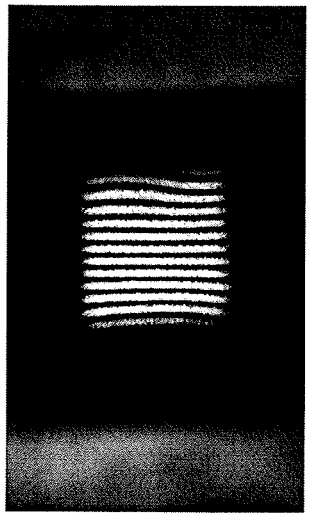
Figure 7C:
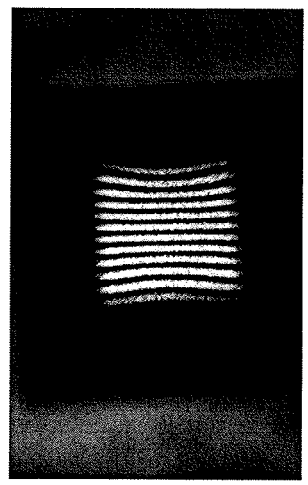

Certain exemplary embodiments of the present invention may be used to measure other physical characteristics of semiconductor devices such as flatness characteristics, crack propagation, amongst others. FIG. 6 illustrates an exemplary thermo-compression bonding machine 600 (with many elements omitted for clarity) including a structured light source 602 (e.g., shown as, but not limited to, digital fringe projector 102). Light source 602 includes grating 604 or other structure (such as a DLP chip in a digital fringe projector embodiment). Light 608 transmitted from source 602 is structured light that includes a structured light pattern imposed on the light, for example, using grate 604. Structured light 608 is received by a diffuser screen 630a. FIG. 6 also illustrates support structure 610 which supports element 612. Element 612 may be, for example, a semiconductor device such as a semiconductor die or other element having a reflective (or at least partially reflective) upper surface 644. Camera 648 images an area within field of view 640 including reflective surface 644 of element 612. This reflection allows camera to image the structured light pattern seen by (and possibly distorted by) element 612. As will be appreciated by those skilled in the art, this type of configuration allows for imaging of a virtual image as shown by reference number 630b. As recited above, the image generated by camera 648 may be used to measure a physical characteristic of the element 612 such as a a flatness characteristic and/or a crack propagation characteristic. FIG. 7A-7C are exemplary images of structured light distorted by various semiconductor devices using the technique illustrated in FIG. 6.

Figure 8:
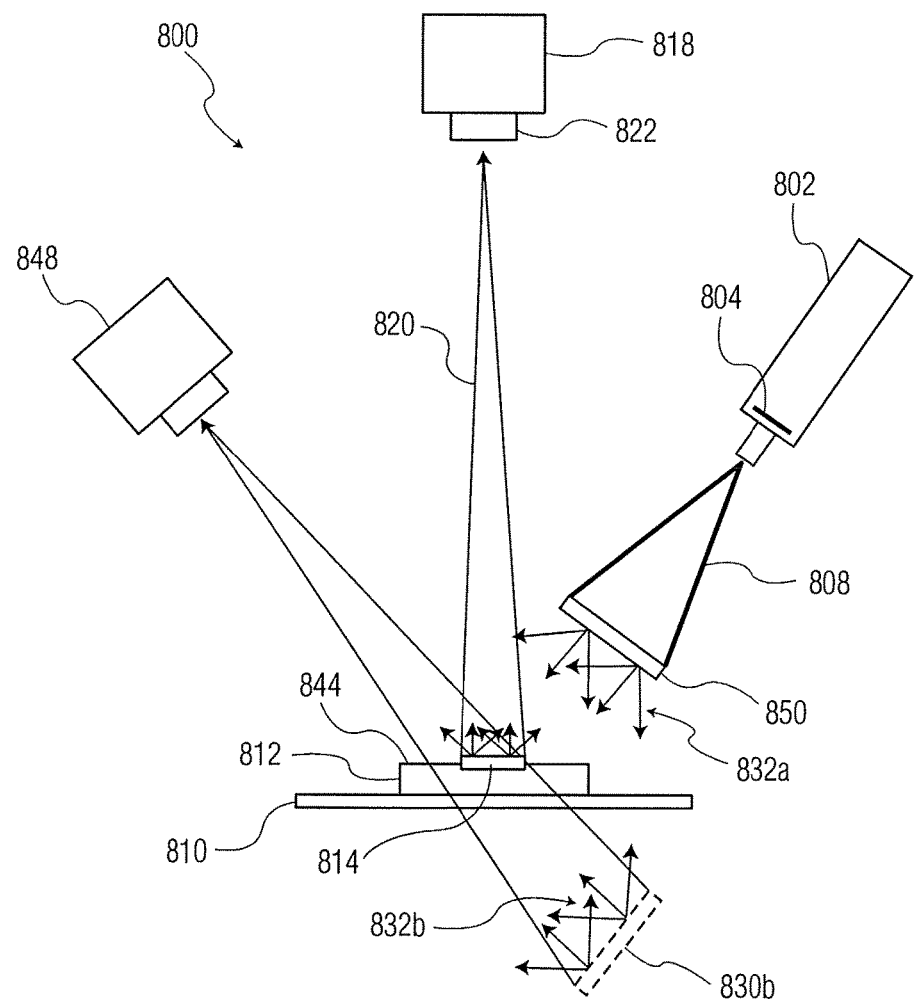
FIG. 8 is another block diagram view of elements of a thermo-compression bonding machine in accordance with an exemplary embodiment of the present invention.

In certain exemplary embodiments of the present invention, it may be desirable to image both a diffusive surface characteristic (e.g., an adhesive material characteristic) and a reflective surface characteristic (e.g., a flatness characteristic). FIG. 8 illustrates elements of a thermo-compression bonding machine 800. Many elements have been omitted for clarity. Machine 800 includes a structured light source 802 (e.g., shown as, but not limited to, digital fringe projector 802). Light source 802 includes grating 804 or other structure (such as a DLP chip in a digital fringe projector embodiment). Light 808 transmitted from source 802 is structured light that includes a structured light pattern imposed on the light, for example, using grate 804. FIG. 8 also illustrates support structure 810 which supports element 812. Element 812 may be, for example, a semiconductor device including a diffusive surface 814 (e.g., an adhesive material) and a reflective surface 844 (e.g., a die surface). Structured light 808 is received by switching diffusive screen 850 (illustrated as, but not limited to, a liquid crystal diffuser screen). When it is desired to image the reflective surface 844, screen 850 may be operated in a diffusive mode, allowing camera 848 to generate an image as described above with respect to FIG. 6, and thereby allowing a physical characteristic (e.g., a flatness characteristic, a crack propagation characteristic, etc.) to be measured. When it is desired to image diffusive surface 814, screen 850 may be operated in a transparent mode, allowing camera 818 to generate an image as described above with respect to FIG. 1, and thereby allowing a physical characteristic (e.g., a volume, a volume distribution, etc.) to be measured.

Although the present invention has been described primarily with respect to imaging using structured lights, it is not limited thereto. Certain aspects of the present invention have applicability to use with other forms and/or configurations of light.

Although the present invention has primarily been described in connection with thermo-compressive bonding machines and processes (e.g., thermo-compressively bonding a first semiconductor device element to another semiconductor device element), it is not limited thereto. For example, the teaching of the present invention have application in conventional die attach systems and methods of using the same.

In certain exemplary embodiments of the present invention described herein, closed loop processes (or feedback driven processes) are described. For example, if a given physical characteristic (e.g., adhesive material volume or distribution) is measured and is not within a predetermined specification (e.g., tolerance), then an aspect of the dispensing process (e.g., the volume of adhesive dispensed, the rate of material dispensed, the temperature of the material dispensed, amongst others) may be adjusted in a closed loop manner. However, it is also within the scope of the present invention to adjust other aspects of the thermo-compression bonding process to in order to achieve the desired physical characteristic specification. Such thermo-compression bonding process aspects that may be adjusted include, for example, bonding temperature, bonding temperature profile, bond force, bonding time, etc.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A thermo-compression bonding machine comprising:
    a bond head assembly for performing a thermo-compression bonding process;
    a dispenser for dispensing an adhesive material onto a first semiconductor device element;

a support structure for supporting the first semiconductor device element including the adhesive material, the thermocompression bonding machine being adapted to bond a second semiconductor device element to the first semiconductor device element, the second semiconductor device element including conductive pillars configured to be thermo-compressively bonded to conductive structures of the first semiconductor device element, the adhesive material being configured to be provided between the first semiconductor device element and the second semiconductor device element;

a structured light source for providing a structured light pattern on the adhesive material;

a camera for creating an image of the structured light pattern on the adhesive material; and image processing hardware and software for analyzing the image to determine a physical characteristic of the adhesive material, and to determine if the physical characteristic is within a predetermined specification.

2. The thermo-compression bonding machine of claim 1 wherein the adhesive material is selected from the group consisting of an epoxy material, a non-conductive paste material, and a curable liquid material.

3. The thermo-compression bonding machine of claim 1 wherein the structured light pattern includes at least one of a parallel bar pattern and a grid pattern.

4. The thermo-compression bonding machine of claim 1 wherein the thermo-compression bonding machine is configured to adjust an aspect of dispensing of the adhesive material by the dispenser for a subsequent semiconductor device element if it is determined that the physical characteristic is not within the predetermined specification, and wherein the aspect is adjusted using a closed loop process whereby the adjusted aspect is determined automatically at least partially based on the determined physical characteristic.

5. The thermo-compression bonding machine of claim 1 wherein the physical characteristic includes at least one of a volume of the adhesive material, and a distribution of a volume of the adhesive material.

6. The thermo-compression bonding machine of claim 1 wherein the thermo-compression bonding machine is configured to adjust an aspect of dispensing of the adhesive material by the dispenser for a subsequent semiconductor device element if it is determined that the physical characteristic is not within the predetermined specification.

7. The thermo-compression bonding machine of claim 1 wherein the adhesive material is a fillet portion of an adhesive provided between the first semiconductor device element and the second semiconductor device element.

8. A thermo-compression bonding machine comprising:
a bond head assembly for performing a thermo-compression bonding process;

a support structure for supporting a first semiconductor device, the thermocompression bonding machine adapted to bond a second semiconductor device element to the first semiconductor device element, the second semiconductor device element including conductive pillars configured to be thermo-compressively bonded to conductive structures of the first semiconductor device element, the adhesive material being configured to be provided between the first semiconductor device element and the second semiconductor device element;

a structured light source for providing a structured light pattern;

a camera for indirectly viewing the structured light pattern using a reflective surface of the first semiconductor device element, the camera generating an image of the structured light pattern; and image processing hardware and software for analyzing the image to determine a flatness characteristic of the first semiconductor device element.

9. The thermo-compression bonding machine of claim 8 wherein the structured light pattern includes at least one of a parallel bar pattern and a grid pattern.

10. The thermo-compression bonding machine of claim 8 wherein the structured light source includes a digital fringe projector.

11. The thermo-compression bonding machine of claim 8 wherein the image processing hardware and software is configured to determine if the flatness characteristic is within a predetermined specification.

12. The thermo-compression bonding machine of claim 8 further comprising a diffuser screen for receiving the structured light pattern from the structured light source.

13. The thermo-compression bonding machine of claim 8 further comprising at least one of a pick tool and a place tool for securing the first semiconductor device element while the camera indirectly views the structured light pattern.

* * * * *